United States Patent
Zhu et al.

(10) Patent No.: US 10,654,820 B2
(45) Date of Patent: May 19, 2020

(54) CRYSTAL FORM OF TASIMELTEON

(71) Applicant: ZHEJIANG JINGXIN PHARMACEUTICAL CO., LTD., Xinchang County, Zhejiang Province (CN)

(72) Inventors: Jianrong Zhu, Xinchang County (CN); Chunyong Peng, Xinchang County (CN); Hongban Zhong, Xinchang County (CN); Xiurong Hu, Xinchang County (CN)

(73) Assignee: ZHEJIANG JINGXIN PHARMACEUTICAL CO., LTD., Shaoxing, Zhejiang (CN)

( * ) Notice: Subject to any disclaimer, the term of this patent is extended or adjusted under 35 U.S.C. 154(b) by 0 days.

(21) Appl. No.: 16/300,303

(22) PCT Filed: Feb. 19, 2017

(86) PCT No.: PCT/CN2017/074030
§ 371 (c)(1),
(2) Date: Nov. 9, 2018

(87) PCT Pub. No.: WO2017/193662
PCT Pub. Date: Nov. 16, 2017

(65) Prior Publication Data
US 2019/0119239 A1    Apr. 25, 2019

(30) Foreign Application Priority Data
May 12, 2016 (CN) ............... 2016 1 0313300

(51) Int. Cl.
| | | |
|---|---|---|
| *C07D 307/79* | (2006.01) |
| *A61K 31/343* | (2006.01) |
| *B01D 9/00* | (2006.01) |
| *A61P 25/20* | (2006.01) |

(52) U.S. Cl.
CPC .......... *C07D 307/79* (2013.01); *A61K 31/343* (2013.01); *B01D 9/0004* (2013.01); *B01D 9/005* (2013.01); *A61P 25/20* (2018.01)

(58) Field of Classification Search
CPC ..... C07D 307/79; B01D 9/0004; B01D 9/005
USPC ....................................................... 514/469
See application file for complete search history.

(56) References Cited

FOREIGN PATENT DOCUMENTS

WO    WO-2017193662 A1 * 11/2017 ........... C07D 307/79

* cited by examiner

*Primary Examiner* — Kahsay Habte
(74) *Attorney, Agent, or Firm* — Proi Intellectual Property US

(57) ABSTRACT

Crystal forms I and II of tasimelteon. Crystal form I: an X-ray powder diffraction spectrum using CuKα radiation and represented by a 2θ angle has diffraction peaks at least at 7.2°±0.2°, 7.9°±0.2°, 10.6°±0.2°, 14.4°±0.2°, 15.9°±0.2°, 17.3°±0.2°, 21.0°±0.2°, 23.2°±0.2°, and 24.4°±0.2°. Crystal form II: an X-ray powder diffraction spectrum using CuKα radiation and represented by a 2θ angle has diffraction peaks at least at 6.8°±0.2°, 12.1°±0.2°, 12.5°±0.2°, 13.1°±0.2°, 13.6°±0.2°, 13.8°±0.2°, 15.8°±0.2°, 17.0°±0.2°, 18.4°±0.2°, 20.8°±0.2°, 24.2°±0.2°, and 24.4°±0.2°. Crystal forms I and II of tasimelteon have advantages of excellent physico-chemical property, good stability and solubility, and simple operation for preparation.

18 Claims, 6 Drawing Sheets

CRYSTAL FORM OF TASIMELTEON

FIELD OF INVENTION

The invention belongs to the field of pharmacy, and specifically relates to the crystal form of tasimelteon, in particular to the crystal forms I and II of tasimelteon and their application in medicine.

BACKGROUND ART

Tasimelteon (Hetlioz™) is a selective agonist at melatonin MT1 and MT2 receptors which are found in high density in the hypothalamic suprachiasmatic nuclei. In January 2014, Tasimelteon was approved by the United States Food and Drug Administration (FDA) for the treatment of Non-24-Hour Sleep-Wake Disorder. Its chemical name is [(1R-2R)—N-[2-(2,3-dihydrobenzofuran-4-yl)cyclopropylmethyl]propanamide], and the molecular formula is $C_{12}H_{19}NO_2$. The structure is as follows:

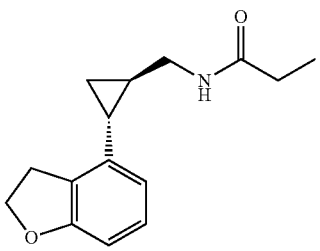 [SMILES: CCC(=O)NC[C@@H]1C[C@H]1c1cccc2c1CCO2]

Non-24, also referred to as Non-24-Hour Sleep-Wake Disorder or Non-24-Hour sleep cycle Disorder, occurs when individuals, primarily blind with no light perception, are unable to synchronize their endogenous circadian pacemaker to the 24-hour light/dark cycle. Individuals with Non-24 have abnormal night sleep patterns, accompanied by difficulty staying awake during the day.

It is estimated that approximately 100,000 people in the United States suffer from Non-24 and cannot feel enough light to set up a normal night sleep schedule, although most people who are completely blind can still feel the light well and can prevent Non-24. Non-24 occurs at any age. Clinical trials in two totally blind subjects diagnosed with non-24 demonstrated the efficacy of Tasimelteon in reducing both nighttime wakefulness and daytime napping. Physiologic monitoring revealed that Tasimelteon resulted in a higher proportion of individuals becoming entrained to the 24-hour cycle compared with placebo.

Patents WO2011009102, CN102675268, CN103087019 and CN104327022 disclose the production methods for Tasimelteon, but don't disclose the crystalline polymorphism of the compound. The patents describe no crystallographic aspect of the compound. In general, active pharmaceutical ingredients (APIs) are capable of existing in polymorphic forms.

Different polymorphs can display marked differences in their key physicochemical and biopharmaceutical performance, including stability, melting point, solubility, dissolution, and so on. These properties can directly affect the production, the storage and the use of APIs and their preparations. Thus, searching for various crystal modifications are essential parts of drug development.

SUMMARY OF THE INVENTION

The present inventors have conducted extensive studies in order to search for various crystal modifications of Tasimelteon, and found that recrystallizing the amorphous form of Tasimelteon form organic solvents can yield two pharmaceutically useful novel crystal forms (form I and form II) with good stability and solubility.

Thus, an object of the present invention is to provide two pharmaceutically useful crystal forms of Tasimelteon.

Another object of the present invention is directed to processes for the preparation of the crystal form I and form II of Tasimelteon.

Another object of the present invention is to provide the use of the above solid forms of Tasimelteon, comprising a single-component crystal form, and/or a multiple-component crystal form, for the manufacture of medicaments, to be used for the treatment of Non-24-Hour Sleep-Wake Disorder.

Another object of the present invention is to provide a pharmaceutical composition comprising the crystal form I and/or the crystal form II of Tasimelteon as active ingredient.

Means for Solving the Problems

[1] The present invention provides the crystal form I of Tasimelteon. Crystal form I: an X-ray powder diffraction spectrum using CuKα radiation and represented by a 2θ angle has diffraction peaks at least at 7.2°±0.2°, 7.9°±0.2°, 10.6°±0.2°, 14.4°±0.2°, 15.9°±0.2°, 17.3°±0.2°, 21.0°±0.2°, 23.2°±0.2°, and 24.4°±0.2°.

[2] Crystal form I as recited in [1] also exhibiting characteristic peaks in X-ray powder diffraction spectrum using CuKα radiation at diffraction angles (2θ) of about 10.8°±0.2°, 16.3°±0.2°, 16.6°±0.2°, 19.7°±0.2°, 21.3°±0.2°, 21.7°±0.2°, 24.1°±0.2°, 24.9°±0.2°, 27.8°±0.2°, 28.3°±0.2° and 30.0°±0.2°.

[3] Crystal form I as recited in [1] is characterized by a differential scanning calorimetry (DSC) plot comprising a melting endothermic event with a peak temperature of 74.2° C. A representative DSC plot for the crystal form I is provided in FIG. 3.

A representative TGA plot for the crystal form I is provided in FIG. 2. The TGA diagram for crystal form I shows no weight loss up to the decomposition temperature (about 200° C.), which proves its good thermal stability. Crystal form I is un-solvated. Crystal form I is anhydrous.

[4] Crystal form I as recited in [1-3] may be prepared by (a) dissolving an amorphous form of Tasimelteon to form a solution with stirring in an organic solvent, or mixtures of an organic solvent and an alkane, mixed in any ratio, or mixtures of water and an organic solvent at 40 to 70° C., preferably at 40 to 60° C. These solvents are used in an amount of 2 to 20 ml, preferably in an amount of 2 to 15 ml, more preferably in an amount of 3 to 10 ml, with respect to 1 g of an amorphous form of Tasimelteon;

(b) cooling the hot solution to 0 to 20° C. rapidly or slowly, preferably to 0 to 5° C., and crystallization;

(c) suction filtering the solvent mixture and drying the polymorph at a temperature 35 to 45° C. for 2 to 4 hours to get the crystal form I of Tasimelteon.

In particular, organic solvent system, including, but not limited to, comprising alcohol (methanol, ethanol, propanol or a mixture of two or more thereof), ketone (acetone, methyl butyl ketone or a mixture of two or more thereof), ester (ethyl acetate, propyl acetate, or a mixture of two or more thereof), ether (tetrahydrofuran, methyl tertbutyl ether, or a mixture of two or more thereof) and chloroform; alkane comprising heptanes, hexane, and pentane; in the mixtures of water and organic solvent, the volume ratio of water is 2% to 20%.

[5] The present invention provides the crystal form II of Tasimelteon. Crystal form II: an X-ray powder diffraction spectrum using CuKα radiation and represented by a 2θ angle has diffraction peaks at least at 6.8°±0.2°, 12.1°±0.2°, 12.5°±0.2°, 13.1°±0.2°, 13.6°±0.2°, 13.8°±0.2°, 15.8°±0.2°, 17.0°±0.2°, 18.4°±0.2°, 20.8°±0.2°, 24.2°±0.2°, and 24.4°±0.2°.

[6] Crystal form II as recited in [5] also exhibiting characteristic peaks in X-ray powder diffraction spectrum using CuKα radiation at diffraction angles (2θ) of about 19.1°±0.2°, 19.9°±0.2°, 20.4°±0.2°, 23.0°±0.2°, 24.7°±0.2°, 25.3°±0.2°, 26.7°±0.2°, 27.1°±0.2° and 28.0°±0.2°.

[7] Crystal form II as recited in [5] is characterized by a differential scanning calorimetry (DSC) plot comprising an endothermic event with a peak temperature of 55.0° C. It is attributed to the release of crystal water from crystal form II. A further melting endothermic event is observed with a peak temperature of 74.3° C. A representative DSC plot for crystal form II is provided in FIG. 7.

A representative TGA plot for crystal form II is provided in FIG. 6. A mass loss of 3.5% of water between room temperature and 80° C. and it means Form II contains 3.5% solvent (water) and it is hydrates. The material began to degrade at approximately 200° C. to show it good thermal stability.

[8] Crystal form II as recited in [5-7] may be prepared by (a) dissolving an amorphous form of Tasimelteon in water, or mixtures of water and organic solvent at 40 to 70° C., preferably at 40 to 60° C. These solvents are used in an amount of 3 to 30 ml, preferably in an amount of 3 to 25 ml, more preferably in an amount of 5 to 20 ml, with respect to 1 g of an amorphous form of Tasimelteon;
(b) cooling the hot solution to 0 to 25° C. slowly, preferably to 0 to 5° C., and crystallization (stirring or static);
(c) suction filtering the solvent mixture and drying the polymorph at a temperature of 35 to 45° C. for 2 to 4 hours to get crystal form II of Tasimelteon.

In particular, organic solvent system, including, but not limited to, comprising alcohol (methanol, ethanol, propanol or a mixture of two or more thereof), ketone (acetone, methyl butyl ketone or a mixture of two or more thereof), acetonitrile, and dimethyl sulfoxide; the mixtures of water and an organic solvent, the volume ratio of the organic solvent is 10% to 60%, preferably, 10% to 50%.

[9] The present invention is also to provide the use of the crystal form I of Tasimelteon, as recited in anyone of [1-3] and/or the crystal form II of Tasimelteon, as recited in anyone of [5-7] for the manufacture of medicaments, to be used for the treatment of Non-24-Hour Sleep-Wake Disorder.

[10] The pharmaceutical composition comprising the crystal form I and/or the crystal form II of Tasimelteon as active ingredient.

Preferably, in addition to a therapeutically effective amount of the crystal form I and/or the crystal form II of Tasimelteon, the above pharmaceutical composition comprises at least one pharmaceutically acceptable excipient or pharmaceutically acceptable carrier. Preferably, the pharmaceutically acceptable excipient comprises a wetting agent, a dispersant, a pH controlling agent, an antioxidant, a filler, a diluent agent, a lubricant, a solubilizer, a suspending agent, a sweetening agent, a binder, a disintegrating agent, an osmotic pressure regulator, a flocculant, an anti adhesive, a suspending agent, an emulsifying agent, an antiseptics or a mixture of two or more thereof.

Equilibrium, solubility, and dissolution rate of the crystal form I and the crystal form II of Tasimelteon are satisfied. The water solubility of the crystal form I was found to be 0.081 mg/ml; and that of the crystal form II of Tasimelteon was 0.104 mg/ml. The crystal form I and the crystal form II of Tasimelteon have a good thermal stability and they are convenient for manufacturing, storage and transportation.

MODES FOR CARRYING OUT THE INVENTION

Figure 1:
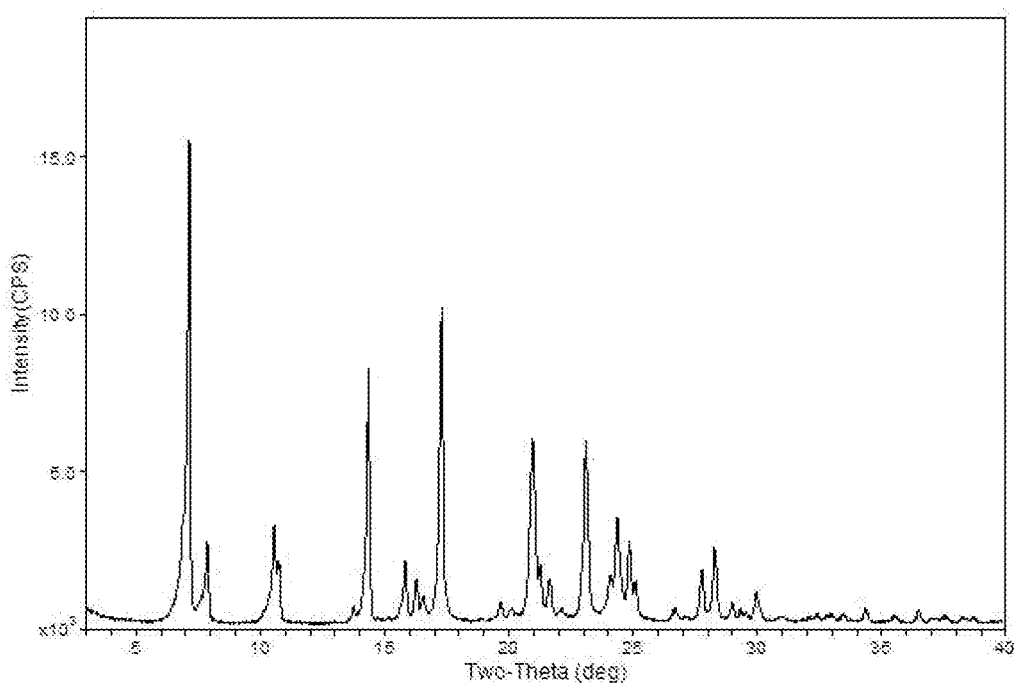
FIG. 1 provides a representative X-ray powder diffraction (XPRD) pattern of the crystal form I of Tasimelteon.

The present invention will be further described below in conjunction with specific embodiments and the accompanying drawings. It should be understood that these examples are for illustrative purposes only, and are not intended to limit the scope of the invention. While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

In the embodiments of the invention, if no specific description is made for the reaction temperature or the operating temperature, the temperature generally refers to room temperature (10-30° C.).

In the embodiments of the present invention, unless otherwise specified, the addition of amount, content and concentration of various substances are mentioned, wherein the percentages refer to the percentage of mass.

In the embodiments of the present invention, when a mixed solvent such as a mixture of two or more organic solvents, a mixed solvent of an organic solvent and water, a percentage of a certain solvent component means a volume percentage (v/v %), for example, an aqueous solution of 20% acetone (20% acetone-water) represents a mixture of 20 volumes of acetone and 80 volumes of water; A 30% acetone solution in n-hexane (30% acetone-n-hexane) represents a mixture of 30 volumes of acetone and 70 volumes of n-hexane.

It is well known in the art, some chemicals are affected by various factors during crystallization, which change the intra-molecular or inter-molecular bonding modes, causing molecular or atoms to be arranged differently in the lattice space to form different polymorphs. Different polymorphs differ in their physical properties such as exterior, solubility, melting point, dissolution rate, bioavailability etc. These can appreciably influence pharmaceutical properties such as stability, bioavailability and clinical efficacy. This phenomenon is particularly evident in oral solid preparations. Polymorph is one of the important factors affecting the quality, clinical efficacy and safety. Therefore, the study of polymorph can help finding the dominant crystalline form, which is beneficial to the clinical efficacy, and the colleague determines the preparation process according to the characteristics of the crystal form. Effectively guaranteeing the drug equivalence of production, and providing reference for formulators in prescription development, new drug design, production process optimization, drug quality control and clinical efficacy.

The crystal form of Tasimelteon can be characterized by XPRD, and the XPRD patterns of the different crystal forms are different, the 2θ angles and/or relative intensity ($I/I_0$) of the diffraction peak expressed will be different.

The invention obtains the crystal form I of Tasimelteon by dissolving Tasimelteon in a specific organic solvent or a mixed solvent with organic solvent and a small amount of water, and crystallization.

The invention provides the crystal form I of Tasimelteon, which exhibits a characteristic X-ray powder diffraction pattern with characteristic peaks expressed in 2θ (°), in d-values (Å) and in relative intensity (%) as given in Table 1

TABLE 1 d-spacing and 2θ angles for form I of Tasimelteon

| NO. | 2θ (°) ± 0.2° | d (Å) | $I/I_0$ (%) |
|---|---|---|---|
| 1 | 7.18 | 12.30 | 100.0 |
| 2 | 7.92 | 11.15 | 16.9 |
| 3 | 10.62 | 8.32 | 20.3 |
| 4 | 10.80 | 8.19 | 12.5 |
| 5 | 14.40 | 6.15 | 52.7 |
| 6 | 15.90 | 5.570 | 11.3 |
| 7 | 16.34 | 5.42 | 7.2 |
| 8 | 16.62 | 5.33 | 3.7 |
| 9 | 17.34 | 5.11 | 64.4 |
| 10 | 19.74 | 4.49 | 3.3 |
| 11 | 21.02 | 4.22 | 36.6 |
| 12 | 21.34 | 4.16 | 10.1 |
| 13 | 21.70 | 4.09 | 6.0 |
| 14 | 23.16 | 3.84 | 36.5 |
| 15 | 24.12 | 3.69 | 7.9 |
| 16 | 24.42 | 3.64 | 20.2 |
| 17 | 24.90 | 3.57 | 16.4 |
| 18 | 25.16 | 3.54 | 8.2 |
| 19 | 27.84 | 3.20 | 10.2 |
| 20 | 28.34 | 3.15 | 14.7 |
| 21 | 29.06 | 3.07 | 3.2 |
| 22 | 30.02 | 2.97 | 5.8 |

It is well known that the same crystal form will have a slightly different X-ray powder diffraction pattern in different test conditions. Factors affecting the X-ray powder diffraction pattern are: crystal purity, crystallinity, particle size of powder sample, sample amount and surface flatness of the powder loaded into the sample holder.

In a preferred embodiment, the crystal form I of Tasimelteon has substantially the same X-ray powder diffraction pattern as the X-ray powder diffraction pattern shown in FIG. 1

It should be understood that the 2θ value of the X-ray powder diffraction pattern may vary slightly between instruments, or between samples, and the values may differ by about 0.2 units (°), or by about 0.1 units (°), so the referenced value cannot be interpreted as absolute value. It should also be understood that the relative intensity of the diffraction peaks may also differ by about 5% or less, and there may be even more differences. Therefore, the intensity of the XPRD trace included in the present invention is illustrative and is not intended to be used for absolute comparison.

In a preferred embodiment, the present invention provides the crystal form I of Tasimelteon. Crystal form I: an X-ray powder diffraction spectrum using CuKα radiation and represented by a 2θ angle has diffraction peaks at least at 7.18°±0.2°, 7.92°±0.2°, 10.62°±0.2°, 14.40°±0.2°, 15.90°±0.2°, 17.34°±0.2°, 21.02°±0.2°, 23.16°±0.2°, and 24.42°±0.2°. Preferred, crystal form I exhibiting characteristic peaks in X-ray powder diffraction spectrum using CuKα radiation at diffraction angles (2θ) of about 7.18°, 7.92°, 10.62°, 14.40°, 15.90°, 17.34°, 21.02°, 23.16°, and 24.42°.

Further, as another preferred embodiment, crystal form I: an X-ray powder diffraction spectrum using CuKα radiation and represented by a 2θ angle has diffraction peaks at least at 10.80°±0.2°, 16.34°±0.2°, 16.62°±0.2°, 19.74°±0.2°, 21.34°±0.2°, 21.70°±0.2°, 24.12±0.2°, 24.90°±0.2°, 27.84°±0.2°, 28.34°±0.2° and 30.02°±0.2°. Preferred, crystal form I exhibiting characteristic peaks in X-ray powder diffraction spectrum using CuKα radiation at diffraction angles (2θ) of about 10.80°, 16.34°, 16.62°, 19.74°, 21.34°, 21.70°, 24.12°, 24.90°, 27.84°, 28.34° and 30.02°.

Further, in a preferred embodiment, crystal form I crystallizes in a monoclinic space group $P2_1$. Its crystallographic parameters are shown in table 2.

TABLE 2

| Crystal system, space group and crystallographic data of Tasimelteon | |
|---|---|
| parameter | Form I |
| Crystal system | monoclinic |
| Space group | $P2_1$ (NO. 4) |
| Crystallographic data | |
| a (Å) | 11.1567 (15) |
| b (Å) | 4.9188 (7) |
| c (Å) | 12.3048 (18) |
| α (°) | 90.00° |
| β (°) | 90.897 (4) |
| γ (°) | 90.00° |
| V (Å$^3$) | 675.17 (17) |
| Z | 2 |
| Chemical formula | $C_{15}H_{19}NO_2$ |
| $\rho_{calcd}$ (mg/m3) | 1.207 |

TABLE 3

Fractional atomic coordinates and isotropic or
equivalent isotropic displacement parameters of crystal form I

| Atom | X | Y | Z | U(eq) |
|---|---|---|---|---|
| $C_1$ | 0.6117(4) | 0.7347(10) | 0.3211(4) | 0.0511(12) |
| $C_2$ | 0.5081(5) | 0.6221(13) | 0.3690(4) | 0.0636(15) |
| $C_3$ | 0.3954(5) | 0.6802(16) | 0.3251(5) | 0.0736(16) |
| $C_4$ | 0.3801(5) | 0.8525(13) | 0.2390(5) | 0.0675(16) |
| $C_5$ | 0.4805(5) | 0.9623(12) | 0.1946(4) | 0.0597(14) |
| $C_6$ | 0.6012(7) | 1.1989(17) | 0.0822(6) | 0.090(2) |
| $C_7$ | 0.6819(6) | 1.0643(11) | 0.1656(4) | 0.0642(16) |
| $C_8$ | 0.5942(4) | 0.9067(11) | 0.2345(4) | 0.0484(11) |
| $C_9$ | 0.7351(4) | 0.6784(11) | 0.3644(4) | 0.0510(12) |
| $C_{10}$ | 0.7601(4) | 0.6578(11) | 0.4852(3) | 0.0473(11) |
| $C_{11}$ | 0.7664(5) | 0.4071(12) | 0.4170(4) | 0.0563(13) |
| $C_{12}$ | 0.8739(5) | 0.7925(11) | 0.5288(4) | 0.0531(13) |
| $C_{13}$ | 0.9283(4) | 0.8699(11) | 0.7200(4) | 0.0535(12) |
| $C_{14}$ | 0.9556(6) | 0.7536(12) | 0.8303(4) | 0.0639(15) |
| $C_{15}$ | 0.8757(8) | 0.865(2) | 0.9167(5) | 0.107(3) |
| N1 | 0.6990(8) | 0.6990(8) | 0.6394(3) | 0.0500(10) |
| O1 | 1.1376(10) | 1.1376(10) | 0.1079(3) | 0.0775(12) |
| O2 | 1.1216(7) | 1.1216(7) | 0.7058(3) | 0.0727(12) |

Figure 4:
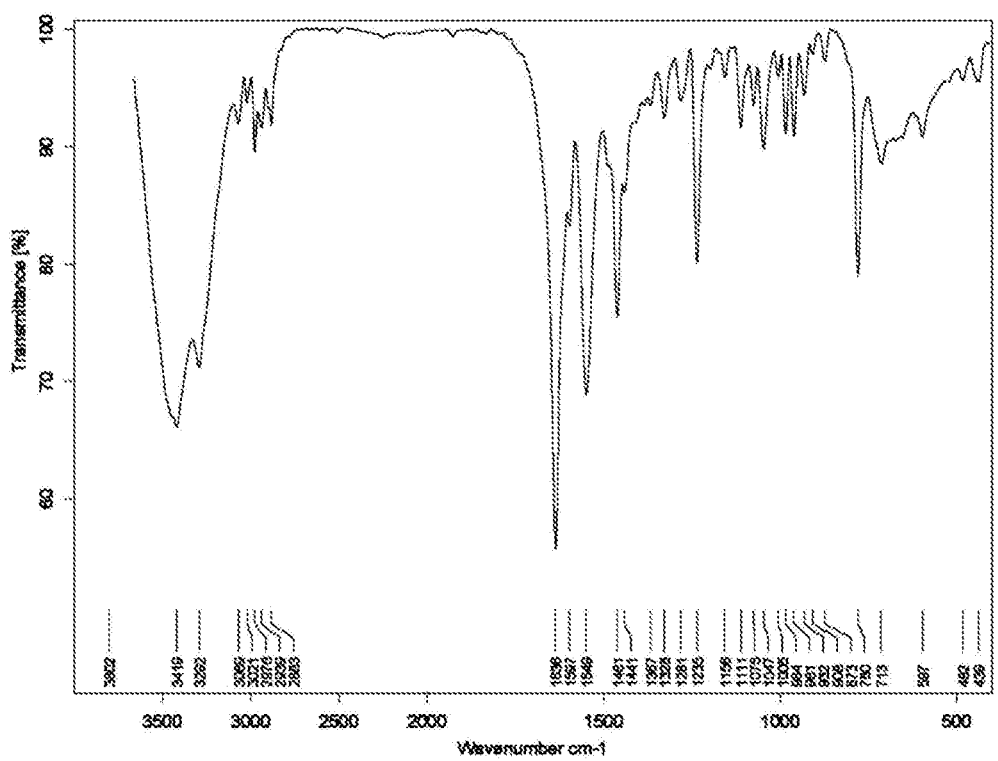
FIG. 4 provides a representative Infrared Fourier spectrum (IR) of the crystal form I of Tasimelteon.

Further, FIG. 4 provides a representative Infrared Fourier spectrum for crystal form I of Tasimelteon which has essentially the following preferred peak at 3419±2 cm$^{-1}$, 3292±2 cm$^1$, 1636±2 cm$^{-1}$, 1549±2 cm$^{-1}$, 1461±2 cm$^{-1}$, 1235±2 cm$^{-1}$, 1075±2 cm$^{-1}$, 1047±2 cm$^{-1}$, 984±2 cm$^1$, 961±2 cm$^{-1}$, 932±2 cm$^{-1}$, 908±2 cm$^{-1}$, 780±2 cm$^{-1}$, 713±2 cm$^{-1}$.

In addition, crystal form I of Tasimelteon is characterized by a DSC plot comprising a melting endothermic event with a peak temperature of 74.2° C. under the heating rate 10° C./min. A representative DSC plot for crystal form I is provided in FIG. 3. It should be understood that there may be similar deviations from the X-ray powder diffraction pattern values, and the values caused by differential scanning calorimetry (DCS) cannot be interpreted as absolute value.

TGA studies (FIG. 2) also showed that no solvent was included in crystal form I, crystal and decomposition started at 200° C., indicating that it has good thermal stability.

Figure 2:
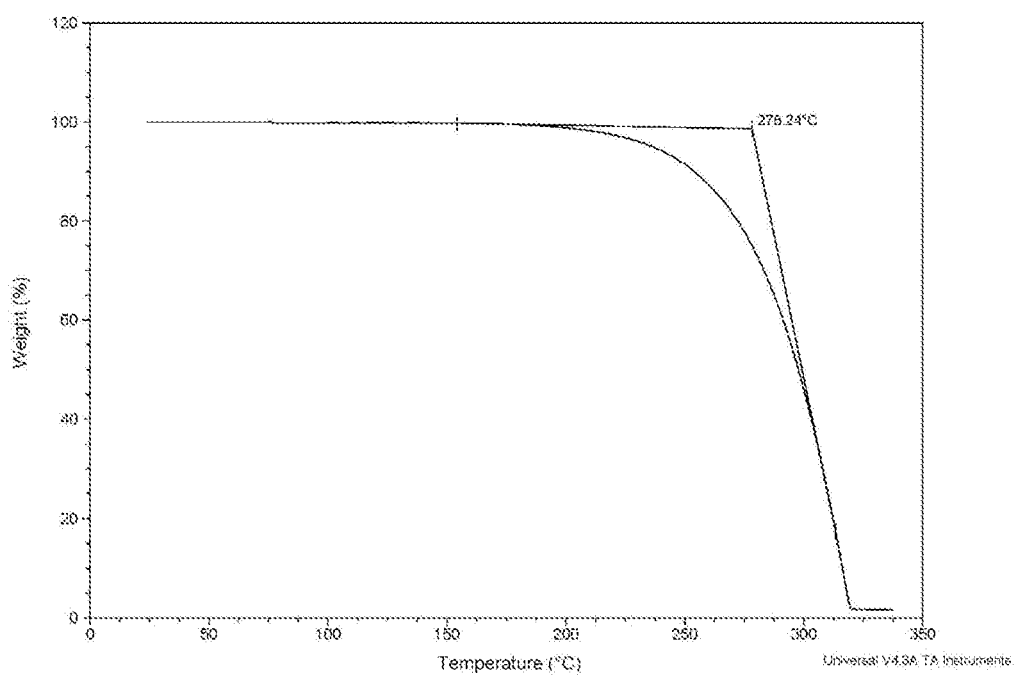
FIG. 2 provides a representative thermal gravimetric analysis (TGA) plot of the crystal form I of Tasimelteon. The X-axis represents temperature (° C.); The Y-axis represents weight (%).
Figure 3:
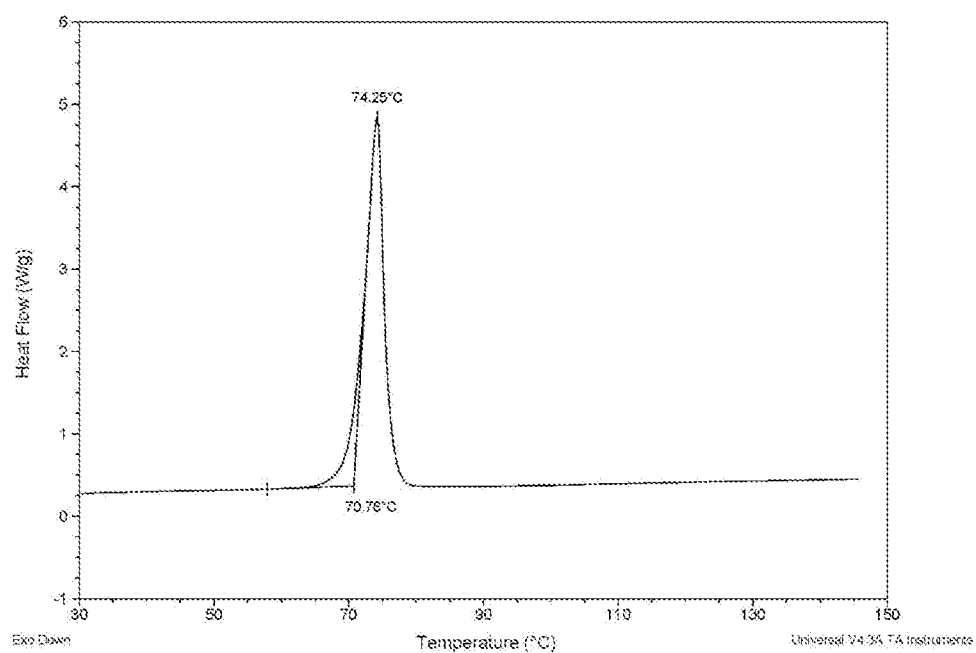
FIG. 3 provides a representative differential scanning calorimetry (DSC) plot of the crystal form I of Tasimelteon. The X-axis represents temperature (° C.); The Y-axis represents heat flow (W/g).

In a preferred embodiment, TGA of crystal form I is substantially the same as FIG. 2, and DSC of crystal form I is substantially the same as FIG. 3.

Meaning of Terms

The term "diffraction peak" refers to a characteristic peak that would not to be attributed to background noise by those skilled in the art.

The term "relative intensity" refers to the peak intensity of the highest intensity, among all the diffraction peaks of the X-ray powder the diffraction pattern is 100%, and the ratio of the intensity of the other peaks refer to the peak intensity of the highest intensity.

It should be understood that in the context of expressing numerical features, the term "about" means that the indicated value may have an error range or floating range of ±5%, ±4%, ±3%, ±2% and ±1%.

The term "substantially the same" means that at least 70%, at least 80%, at least 90%, at least 95% or at least 99% of the peaks in the X-ray powder diffraction pattern appear in the exemplary X-ray powder diffraction pattern given.

The invention obtains the crystal form II of Tasimelteon by dissolving Tasimelteon in water or a mixed solvent with organic solvent and water, heating, stirring, cooling and crystallization.

The invention provides the crystal form II of Tasimelteon, which exhibits a characteristic X-ray powder diffraction pattern with characteristic peaks expressed in 2θ (°), in d-values (Å) and in relative intensity (%) as given in Table 4.

TABLE 4 d-spacing and 2θ angles for crystal form II of Tasimelteon

| NO. | 2θ (°) (±0.2°) | d (Å) | I/I$_0$ (%) |
|---|---|---|---|
| 1 | 6.79 | 13.00 | 100.0 |
| 2 | 12.14 | 7.28 | 5.3 |
| 3 | 12.50 | 7.08 | 2.0 |
| 4 | 13.06 | 6.77 | 3.5 |
| 5 | 13.60 | 6.51 | 13.5 |
| 6 | 13.82 | 6.40 | 11.5 |
| 7 | 15.78 | 5.61 | 5.9 |
| 8 | 17.04 | 5.20 | 6.3 |
| 9 | 17.60 | 5.04 | 2.5 |
| 10 | 18.36 | 4.83 | 45.0 |
| 11 | 19.06 | 4.65 | 2.5 |
| 12 | 19.88 | 4.46 | 4.6 |
| 13 | 20.44 | 4.34 | 7.7 |
| 14 | 20.82 | 4.26 | 17.8 |
| 15 | 22.98 | 3.87 | 4.1 |
| 16 | 24.20 | 3.68 | 14.6 |
| 17 | 24.42 | 3.64 | 16.3 |
| 18 | 24.72 | 3.60 | 7.6 |
| 19 | 25.30 | 3.52 | 3.9 |
| 20 | 26.74 | 3.33 | 5.3 |
| 21 | 27.08 | 3.29 | 5.7 |
| 22 | 27.32 | 3.26 | 2.9 |
| 23 | 27.96 | 3.19 | 3.5 |
| 24 | 29.00 | 3.08 | 3.3 |
| 25 | 29.66 | 3.01 | 2.3 |
| 26 | 30.76 | 2.90 | 2.2 |

Figure 5:
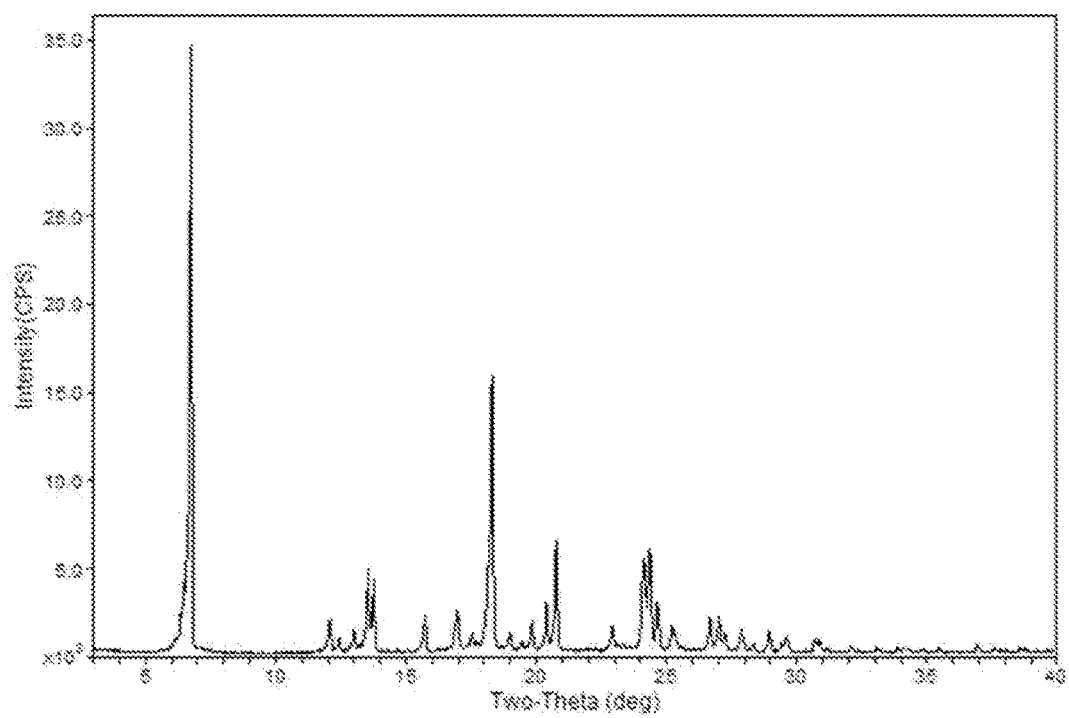
FIG. 5 provides a representative X-ray powder diffraction (XPRD) pattern of the crystal form II of Tasimelteon.

It is well known that the same crystal form will have a slightly different X-ray powder diffraction pattern in different test conditions. Factors affecting the X-ray powder diffraction pattern are: crystal purity, crystallinity, particle size of powder sample, sample amount and surface flatness of the powder loaded into the sample holder. In a preferred embodiment, the crystal form II of Tasimelteon has substantially the same X-ray powder diffraction pattern as the X-ray powder diffraction pattern shown in FIG. 5.

It should be understood that the 2θ value of the X-ray powder diffraction pattern may vary slightly between instruments, or between samples, and the values may differ by about 0.2 units (°), or by about 0.1 units (°), so the referenced value cannot be interpreted as absolute value. It should also be understood that the relative intensity of the diffraction peaks may also differ by about 5% or less, and there may be even more differences. Therefore, the intensity of the PXRD trace included in the present invention is illustrative and is not intended to be used for absolute comparison. In a preferred embodiment, the present invention provides the crystal form II of Tasimelteon. Crystal form II: an X-ray powder diffraction spectrum using CuKα radiation and represented by a 2θ (±0.2°) angle has diffraction peaks at least at 6.79°, 12.14°, 13.60°, 13.82°, 15.78°, 17.04°, 18.36°, 20.82°, 24.20° and 24.42°. Further, as another preferred embodiment, crystal form I: an X-ray powder diffraction spectrum using CuKα radiation and represented by a 2θ (±0.2°) angle has diffraction peaks at least at 19.060, 19.88°, 20.44°, 22.98°, 24.72°, 25.30°, 26.74°, 27.08°, 27.96°.

Figure 10:
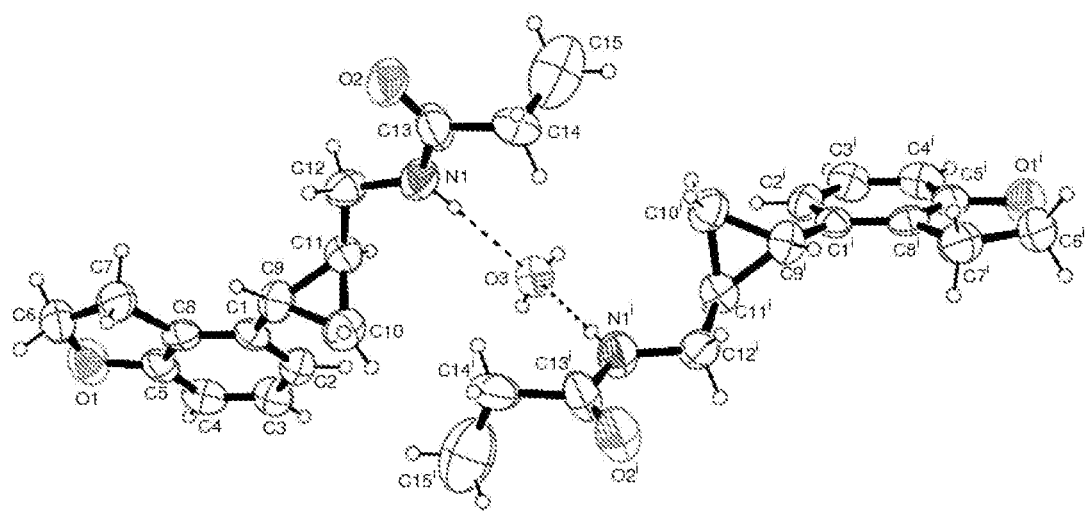

Further, in a preferred embodiment, crystal form II crystallizes in a tetragonal space group P4$_3$2$_1$2. Its crystallographic parameters are shown in table 5. A minimum symmetrical unit contains one Tasimelteon molecule and half of a water molecule connected by hydrogen bond. FIG. 10 shows the absolute configuration model of crystal form II of Tasimelteon. Structure analysis of the form shows that water molecule is hydrogen bonded to four Tasimelteon molecules, and thus the crystal water is very stable.

TABLE 5

Crystal system, space group and crystallographic data of crystal form II of Tasimelteon

| Parameter | Form II |
|---|---|
| Crystal system | tetragonal |
| Space group | P4$_3$2$_1$2 (NO. 92) |
| Crystallographic data | |
| a (Å) | 7.3451 (5) |
| b (Å) | 7.3451 (5) |
| c (Å) | 52.038 (4) |
| α (°) | 90.00 |
| β (°) | 90.00 |
| γ (°) | 90.00 |
| V(Å$^3$) | 2807.5 (3) |
| Z | 4 |
| Chemical formula | C$_{15}$H$_{19}$NO$_2$•0.5H$_2$O |
| ρ$_{calcd}$ (mg/m3) | 1.203 |

TABLE 6

Fractional atomic coordinates and isotropic or equivalent isotropic displacement parameters of crystal form II

| Atom | X | Y | Z | U(eq) |
|---|---|---|---|---|
| C$_1$ | X0.4681(8) | 0.4659(7) | 0.39297(10) | 0.0402(13) |
| C$_2$ | 0.6375(9) | 0.5155(8) | 0.40256(12) | 0.0471(15) |
| C$_3$ | 0.7728(9) | 0.5800(9) | 0.38684(12) | 0.0569(17) |
| C$_4$ | 0.7466(9) | 0.6001(9) | 0.36087(14) | 0.0565(16) |
| C$_5$ | 0.5788(10) | 0.5520(8) | 0.35165(11) | 0.0503(16) |
| C$_6$ | 0.3425(12) | 0.5101(11) | 0.32394(13) | 0.072(2) |
| C$_7$ | 0.2750(10) | 0.4538(10) | 0.35051(13) | 0.0619(18) |
| C$_8$ | 0.4421(8) | 0.4852(7) | 0.36704(11) | 0.0428(14) |
| C$_9$ | 0.3219(9) | 0.3884(9) | 0.40908(11) | 0.0511(16) |
| C$_{10}$ | 0.3651(10) | 0.2800(10) | 0.43314(12) | 0.0605(18) |
| C$_{11}$ | 0.2741(8) | 0.4664(9) | 0.43527(12) | 0.0499(15) |
| C$_{12}$ | 0.0800(9) | 0.4729(10) | 0.44376(11) | 0.0541(16) |
| C$_{13}$ | −0.0940(11) | 0.4069(11) | 0.48279(12) | 0.067(2) |
| C$_{14}$ | −0.0869(13) | 0.3500(12) | 0.51128(14) | 0.085(2) |
| C$_{15}$ | −0.1133(18) | 0.5072(12) | 0.5262(2) | 0.130 |
| N1 | 0.0676(8) | 0.4331(9) | 0.47107(9) | 0.0635(16) |
| O1 | 0.5301(8) | 0.5638(7) | 0.32587(9) | 0.0756(16) |
| O2 | −0.2372(7) | 0.4219(9) | 0.47158(9) | 0.0802(17) |
| O3 | 0.4252(6) | 0.4252(6) | 0.5000 | 0.0538(15) |

Figure 8:
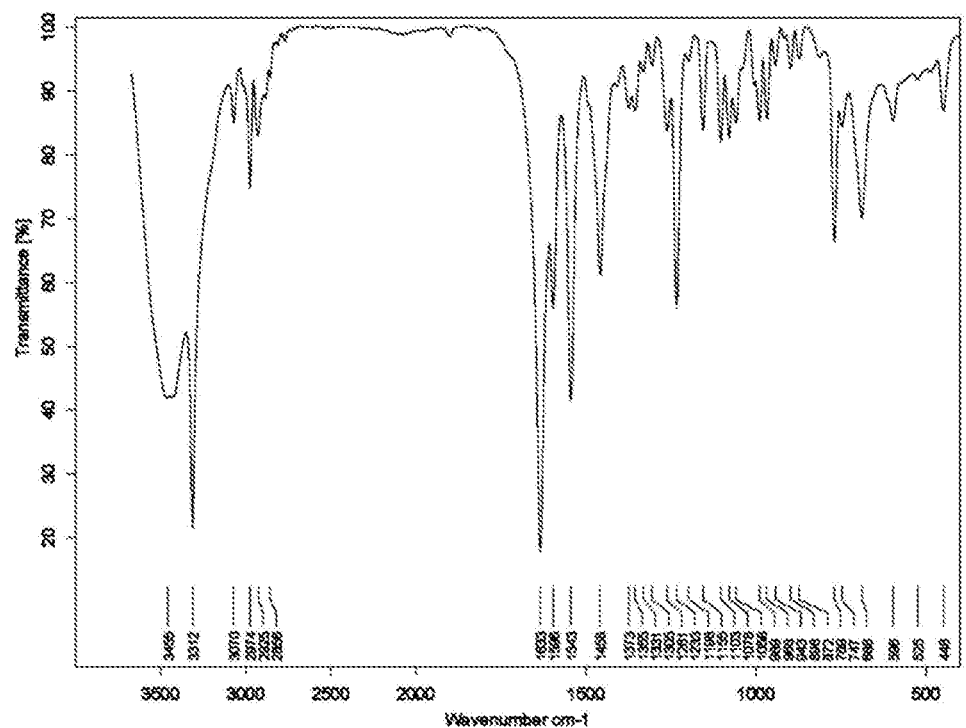
FIG. 8 provides a representative Infrared Fourier spectrum (IR) of the crystal form II of Tasimelteon.

Further, FIG. 8 provides a representative Infrared Fourier spectrum for crystal form II of Tasimelteon which, has essentially the following preferred peak at 3455±2 cm$^{-1}$, 3312±2 cm$^{-1}$, 2974±2 cm$^{-1}$, 1633±2 cm$^{-1}$, 1596±2 cm$^{-1}$, 1543±2 cm$^{-1}$, 1458±2 cm$^{-1}$, 1233±2 cm$^{-1}$, 1155±2 cm$^{-1}$, 989±2 cm$^{-1}$, 968±2 cm$^{-1}$, 943±2 cm$^{-1}$, 898±2 cm$^{-1}$, 872±2 cm$^{-1}$, 769±2 cm$^{-1}$, 747±2 cm$^{-1}$, 688±2 cm$^{-1}$, 596±2 cm$^{-1}$, 4482 cm$^{-1}$.

In addition, crystal form II of Tasimelteon is characterized by a DSC plot with 10° C./min heating rate comprising an endothermic event with a peak temperature of 55.0° C. It is attributed to the release of crystal water (corresponds to 0.5 mol of water) from crystal form II. A further melting endothermic event is observed with a peak temperature of 74.3° C. A representative DSC plot for crystal form II is provided in FIG. 7. It should be understood that there may be similar deviations from the X-ray powder diffraction pattern values, and the values caused by differential scanning calorimetry (DCS) cannot be interpreted as absolute value.

Figure 6:
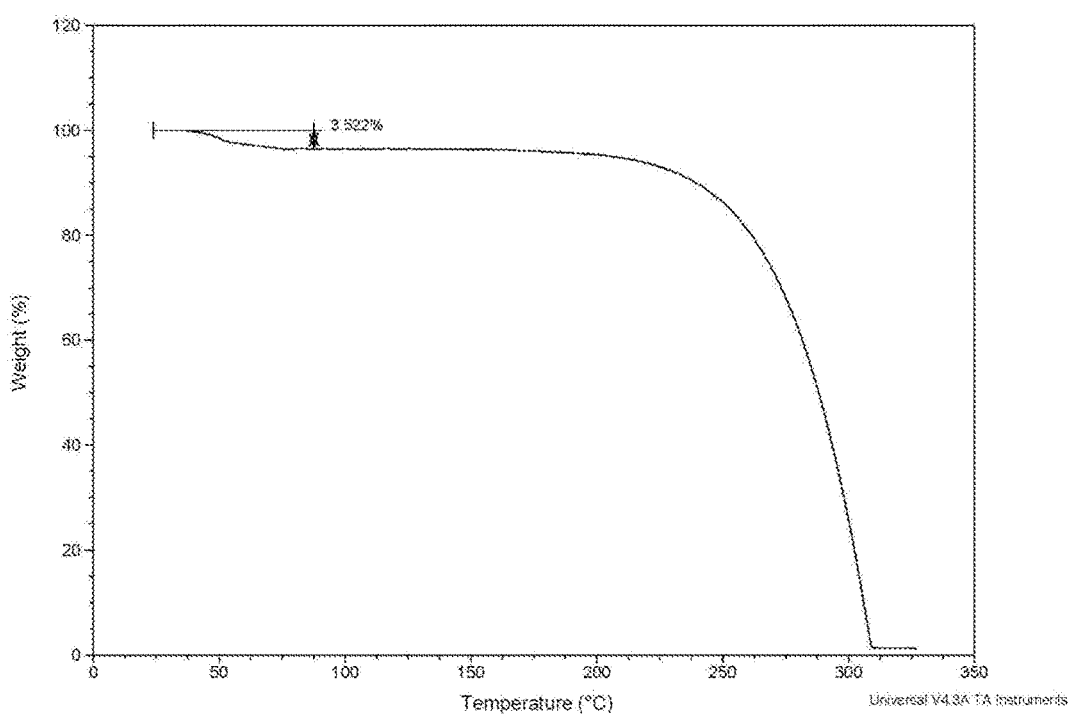
FIG. 6 provides a representative thermal gravimetric analysis (TGA) plot of the crystal form II of Tasimelteon. The X-axis represents temperature (° C.); The Y-axis represents weight (%).

A representative TGA plot for crystal form II is provided in FIG. 6. A mass loss of 3.5% corresponds to 0.5 mol of water between room temperature and 80° C., which matched excellently with the theoretical value of 0.5 mol water per mole Tasimelteon. No further weight loss was observed until the material began to degrade at approximately 200° C., indicating that it has good thermal stability.

Figure 7:
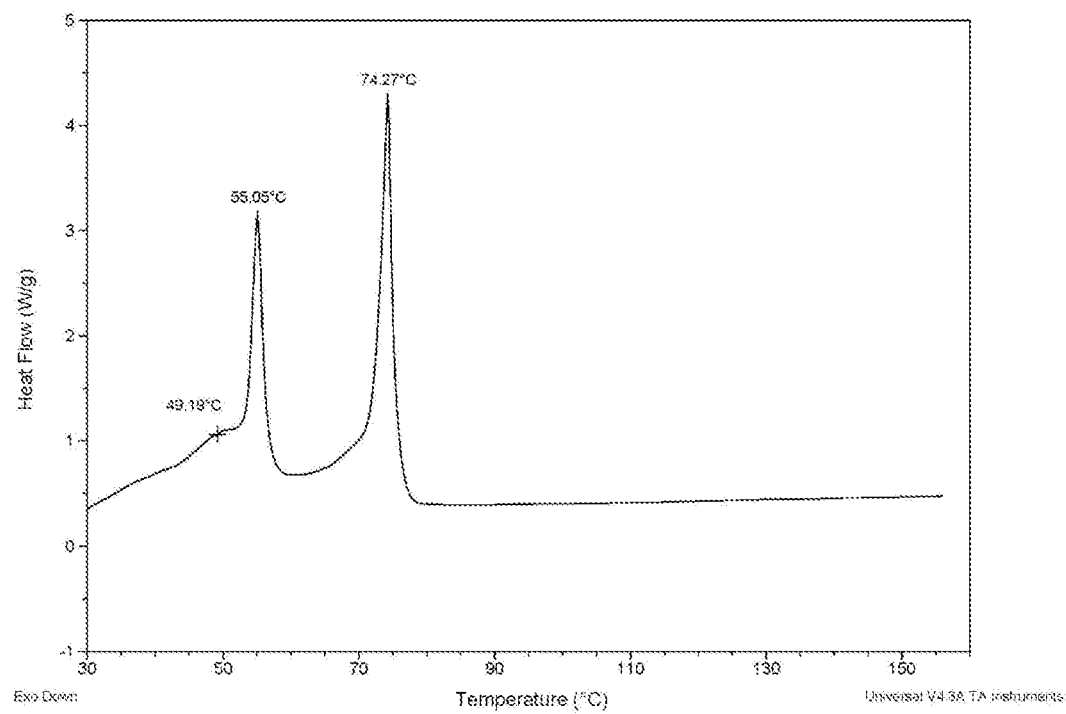
FIG. 7 provides a representative differential scanning calorimetry (DSC) plot of the crystal form II of Tasimelteon. The X-axis represents temperature (° C.); The Y-axis represents heat flow (W/g).

In a preferred embodiment, TGA of crystal form II is substantially the same as FIG. 6, and DSC of crystal form II is substantially the same as FIG. 7.

Meaning of Terms

The term "diffraction peak" refers to a characteristic peak that would not to be attributed to background noise by those skilled in the art.

The term "relative intensity" refers to the peak intensity of the highest intensity among all the diffraction peaks of the X-ray powder, the diffraction pattern is 100%, and the ratio of the intensity of the other peaks refers to the peak intensity of the highest intensity It should be understood that in the context of expressing numerical features, the term "about" means that the indicated value may have an error range or floating range of ±5%, ±4%, ±3%, ±2% and +1%.

The term "substantially the same" means that at least 70%, at least 80%, at least 90%, at least 95% or at least 99% of the peaks in the X-ray powder diffraction pattern appear in the exemplary X-ray powder diffraction pattern given.

Similar to polymorphs, non-solvent compounds and solvent compounds, including hydrates, exhibit different physical properties and behaviors. Solvent compounds, including hydrates (hydrate crystal form), are also a common form of drug presence in the chemical and pharmaceutical industries. The crystal form II is a hydrate crystal form. The crystal form II contained one molecules of TSM and half molecule of water.

The water solubility of the crystal form I was found to be 0.081 mg/ml; and that of the crystal form II 0.104 mg/ml. Intrinsic dissolution studies in water shows both crystal forms have a good dissolution rate, especially for crystal form II compared to form I.

In the pharmaceutical composition of the present invention, a pharmaceutically acceptable excipient or a pharmaceutically acceptable carrier is included. In the present invention, the excipient refers to other than API in the pharmaceutical preparation. For example, a binder, fillers, a disintegrating agent, a lubricant in tablets; matrix part in semisolid preparation; an antiseptic, an antioxidant, a flavoring agent, a fragrance, a cosolvent, an emulsifying agent, a solubilizer, an osmotic pressure regulator, a colorant in liquid preparation. Preferably, the excipient in the present invention is a wetting agent, a dispersant, a pH controlling agent, an antioxygen, a filler, a diluent agent, a lubricant, a solubilizer, a suspending agent, a sweetening agent, a binder, a disintegrating agent, an osmotic pressure regulator, a flocculant, a flocculant, an antiadhesive, an emulsifying agent, an antiseptics or a mixture of two or more thereof; more preferred, fillers, a diluent agent, a disintegrating agent, a lubricant, a disintegrating agent, a wetting agent, a binder or a mixture of two or more thereof; more preferred, the filler is preferably starch, such as pregelatinized starch, microcrystalline cellulose, lactose, calcium hydrogen phosphate, or a mixture of two or more thereof; the lubricant is preferably magnesium stearate, talcum powder, silica, or a mixture of two or more thereof; the lubricant agent is preferably magnesium stearate, talcum powder or silicon dioxide. The disintegrating agent is preferably dry starch, sodium carboxymethyl cellulose, cross-linked povidone or a mixture of two or more thereof; the adhesive is preferably starch paste, methylcellulose, hydroxypropyl cellulose, gelatin or a mixture of two or more thereof. The particular type and amount of the pharmaceutically acceptable excipient or pharmaceutically acceptable carrier can be screened according to common knowledge in the art or determined by simple experimentation.

The pharmaceutical composition of the present invention can be formulated into conventional forms well known to those skilled in the art, and the chosen method of preparation will depend on the intended route of administration. For example, as an oral administration, it may be in the form of a tablet, a capsule, a micro-capsule, a pill, pellets, powder, a sustained release formulation, a solution or a suspension; as a parenteral injection, it may be in the form of a sterile, a suspension or an emulsion; as a topical administration, it may be in the form of ointment or cream; as a rectal administration, it may be in the form of suppository.

WORKING EXAMPLES

Materials: the solvents were of analytical grade, and were purchased from Sinopharm Chemical Reagent Co. Ltd. and used as received.

The amorphous form of Tasimelteon can be prepared according to the methods described in WO2011009102, but is not limited to this method.
Methods:
Powder X-Ray Diffraction (XPRD):

The diffraction patterns were measured on Rigaku D/Max-2550PC diffractometer using a rotating-anode Cu-target X-ray ($\lambda$=1.5406 Å) generator operated at 40 kV and 250 mA. The scans were run from 3 to 500 (2θ) of θ~2°, with an increasing step size of 0.02° and scanning rate of 5°/min.
Differential Scanning Calorimetry (DSC)

The DSC analysis was performed on a TA DSC Q100 differential scanning calorimeter, and the heating was carried out at rate of 10° C./min under a nitrogen flow of 50 ml/min. A temperature range of 30° C.-150° C. was scanned.
Thermogravimetric Analysis (TGA)

TGA was performed on a TA instruments SDT Q600 thermogravimetric analyzer. The samples were heated over the temperature range room temperature of 30-365° C. at a constant heating rate of 10° C./min. The samples were purged with a stream of flowing nitrogen at 120 ml/min throughout the experiment.

Example 1 Preparation of Crystal Form I

In room temperature, Tasimelteon (1 g) was added to 6 ml methanol, and the mixture was stirred at 50° C. until all dissolved. The thus obtained solution was cooled to 0 to 5° C., stirred for 1-2 hours, and the precipitated crystals were recovered through filtration, and dried in the vacuum dryer at 40° C. for 2 hours, to thereby yield 0.6 g crystal form I of Tasimelteon.

Example 2 Preparation of Crystal Form I

In room temperature, Tasimelteon (0.5 g) was added to 5 ml ethanol, and the mixture was stirred at 40° C. until all dissolved. The thus obtained solution was cooled to 5 to 10° C., stirred for 1 hours, and the precipitated crystals were recovered through filtration, and dried in the vacuum dryer at 35° C. for 2 hours, to thereby yield 0.35 g crystal form I of Tasimelteon.

Example 3 Preparation of Crystal Form I

In room temperature, Tasimelteon (5 g) was added to 10 ml acetone, and the mixture was stirred at 50° C. until all dissolved. The thus obtained solution was cooled to 0 to 5° C., and the precipitated crystals were recovered through filtration, and dried in the vacuum dryer at 45° C. for 2 hours, to thereby yield 4.75 g crystal form I of Tasimelteon.

Example 4 Preparation of Crystal Form I

In room temperature, Tasimelteon (0.5 g) was added to 3 ml ethyl acetate, and the mixture was stirred at 50° C. until all dissolved. The thus obtained solution was cooled to 5 to 10° C., static crystallization for 2 hours, and the precipitated crystals were recovered through filtration, and dried in the vacuum dryer at 40° C. for 3 hours, to thereby yield 0.25 g crystal form I of Tasimelteon.

Example 5 Preparation of Crystal Form I

In room temperature, Tasimelteon (10 g) was added to 20 ml tetrahydrofuran, and the mixture was stirred at 60° C. until all dissolved. The thus obtained solution was cooled to 5 to 10° C., stirred for 1-3 hours, and the precipitated crystals were recovered through filtration, and dried in the vacuum dryer at 40° C. for 2 hours, to thereby yield 7.8 g crystal form I of Tasimelteon.

Example 6 Preparation of Crystal Form I

In room temperature, Tasimelteon (5 g) was added to 20 ml methyl tertbutyl ether, and the mixture was stirred at 50° C. until all dissolved. The thus obtained solution was rapidly cooled to 10 to 15° C., stirred for 1 hours, and the precipitated crystals were recovered through filtration, and dried in the vacuum dryer at 35° C. for 2 hours, to thereby yield 3.6 g crystal form I of Tasimelteon.

Example 7 Preparation of Crystal Form I

In room temperature, Tasimelteon (10 g) was added to 50 ml chloroform, and the mixture was stirred at 50° C. until all dissolved. The thus obtained solution was rapidly cooled to 5 to 10° C., stirred for 2 hours, and the precipitated crystals were recovered through filtration, and dried in the vacuum dryer at 45° C. for 2 hours, to thereby yield 6.5 g crystal form I of Tasimelteon.

Example 8 Preparation of Crystal Form I

In room temperature, Tasimelteon (20 g) was added to 150 ml 90% methanol-water (v:v=ml:ml), and the mixture was stirred at 60° C. until all dissolved. The thus obtained solution was rapidly cooled to 0 to 5° C., stirred for 3-4 hours, and the precipitated crystals were recovered through filtration, and dried in the vacuum dryer at 40° C. for 3 hours, to thereby yield 12.5 g crystal form I of Tasimelteon.

Example 9 Preparation of Crystal Form I

In room temperature, Tasimelteon (3 g) was added to 30 ml 90% ethanol-water (v:v=ml:ml), and the mixture was stirred at 60° C. until all dissolved. The thus obtained solution was rapidly cooled to 0 to 5° C., static crystallization, and the precipitated crystals were recovered through filtration, and dried in the vacuum dryer at 45° C. for 2 hours, to thereby yield 1.2 g crystal form I of Tasimelteon.

Example 10 Preparation of Crystal Form I

Tasimelteon (2 g) was added to 20 ml 50% ethyl acetate-hexane (v:v=ml:ml), and the mixture was stirred at 50° C. until all dissolved. The thus obtained solution was cooled to 5 to 10° C., stirring crystallization, and the precipitated crystals were recovered through filtration, and dried in the vacuum dryer at 40° C. for 4 hours, to thereby yield 1.7 g crystal form I of Tasimelteon.

Example 11 Preparation of Crystal Form I

Tasimelteon (5 g) was added to 20 ml 80% acetone-water (v:v=ml:ml), and the mixture was stirred at 50° C. until all dissolved. The thus-obtained solution was cooled to 10 to 15° C., stirring crystallization, and the precipitated crystals were recovered through filtration, and dried in the vacuum dryer at 45° C. for 4 hours, to thereby yield 4.2 g crystal form I of Tasimelteon.

Example 12 Preparation of Crystal Form II

In room temperature, Tasimelteon (2 g) was added to 40 ml water, and the mixture was stirred at 50° C. until all dissolved. The thus obtained solution was cooled to room temperature (about 15 to 20° C.), stirring crystallization, and the precipitated crystals were recovered through filtration, and dried in the vacuum dryer at 35° C. for 3 hours, to thereby yield 1.8 g crystal form II of Tasimelteon.

Example 13 Preparation of Crystal Form II

In room temperature, Tasimelteon (5 g) was added to 15 ml 20% acetonitrile-water (v:v=ml:ml), and the mixture was stirred at 40° C. until all dissolved. The thus obtained solution was cooled to 5 to 10° C., stirring crystallization, and the precipitated crystals were recovered through filtration, and dried in the vacuum dryer at 40° C. for 4 hours, to thereby yield 4.1 g crystal form II of Tasimelteon.

Example 14 Preparation of Crystal Form II

In room temperature, Tasimelteon (2 g) was added to 40 ml 20% methanol-water (v:v=ml:ml), and the mixture was stirred at 50° C. until all dissolved. The thus obtained solution was cooled to 10 to 15° C., stirring crystallization, and the precipitated crystals were recovered through filtration, and dried in the vacuum dryer at 35° C. for 3 hours, to thereby yield 1.8 g crystal form II of Tasimelteon.

Example 15 Preparation of Crystal Form II

In room temperature, Tasimelteon (5 g) was added to 80 ml 50% methanol-water (v:v=ml:ml), and the mixture was stirred at 50° C. The thus-obtained solution was cooled to 5 to 10° C., stirring crystallization, and the precipitated crystals were recovered through filtration, and dried in the vacuum dryer at 40° C. for 2 hours, to thereby yield 4.7 g crystal form II of Tasimelteon.

Example 16 Preparation of Crystal Form II

In room temperature, Tasimelteon (5 g) was added to 100 ml 10% ethanol-water (v:v=ml:ml), and the mixture was stirred at 50° C. until all dissolved. The thus obtained solution was cooled to 0 to 5° C., stirring crystallization, and the precipitated crystals were recovered through filtration, and dried in the vacuum dryer at 40° C. for 4 hours, to thereby yield 4.5 g crystal form II of Tasimelteon.

Example 17 Preparation of Crystal Form II

In room temperature, Tasimelteon (5 g) was added to 50 ml 50% ethanol-water (v:v=ml:ml), and the mixture was stirred at 50° C. until all dissolved. The thus obtained solution was cooled to 5 to 10° C., stirring crystallization, and the precipitated crystals were recovered through filtration, and dried in the vacuum dryer at 40° C. for 2 hours, to thereby yield 4.5 g crystal form II of Tasimelteon.

Example 18 Preparation of Crystal Form II

In room temperature, Tasimelteon (2 g) was added to 50 ml 20% acetone-water (v:v=ml:ml), and the mixture was stirred at 40° C. The thus obtained solution was cooled to 0 to 5° C., static crystallization, and the precipitated crystals were recovered through filtration, and dried in the vacuum dryer at 40° C. for 4 hours, to thereby yield 1.8 g crystal form II of Tasimelteon.

Example 19 Preparation of Crystal Form II

In room temperature, Tasimelteon (8 g) was added to 40 ml 50% acetone-water (v:v=ml:ml), and the mixture was stirred at 50° C. The thus obtained solution was cooled to 5 to 10° C., stirring for 2-4 hours, and the precipitated crystals were recovered through filtration, and dried in the vacuum dryer at 40° C. for 2 hours, to thereby yield 6.8 g crystal form II of Tasimelteon.

Example 20 Preparation of Crystal Form II

In room temperature, Tasimelteon (2 g) was added to 25 ml 30% acetonitrile-water (v:v=ml:ml), and the mixture was stirred at 40° C. The thus obtained solution was cooled to 0 to 5° C., static crystallized, and the precipitated crystals were recovered through filtration, and dried in the vacuum dryer at 40° C. for 4 hours, to thereby yield 1.6 g crystal form II of Tasimelteon.

Example 21 Preparation of Crystal Form II

In room temperature, Tasimelteon (3 g) was added to 10 ml 10% DMSO-water (v:v=ml:ml), and the mixture was stirred at 50° C. The thus obtained solution was cooled, stirring for 2-3 hours, and the precipitated crystals were recovered through filtration, and dried in the vacuum dryer at 40° C. for 2 hours, to thereby yield 2.7 g crystal form II of Tasimelteon.

Example 22 Solubility in Water at 37° C.

Move 25 ml water into a 50 ml eggplant bottle separately, add crystal form I and crystal form II Tasimelteon separately, stir in a constant temperature oil bath to balance for 72 hours, and then filtrate by 0.45 microporous membrane. The filtrate is diluted by water. The water solubilities of crystal form I and crystal form II at 37° C. were determined by calculating each sample concentration of its saturated solution determined through measuring absorbance at $\lambda_{max}$ (281 nm). Standard curve method is used to calculate the equilibrium solubility.

The result shows the water solubility of crystal form I was found to be 0.081 mg/ml; and that of the crystal form II 0.104 mg/ml.

Example 23 Intrinsic Dissolution Studies 200 mg of crystal form I or crystal form II was taken in the intrinsic attachment and compressed to a 1.33 cm² and 0.1 cm thick of disk using a hydraulic press at a pressure of 9 MPa for 60 s. The intrinsic attachment was placed in a jar of 100 mL of water to 37° C. and rotated at 150 r.p.m. 1 milliliter of the aliquot each is collected at specific time intervals and blank medium of the same volume and temperature is added, and the absorbance at max (281 nm) is measured, and the cumulative dissolution rate is calculated to plot the concentration-time standard curves of the respective compounds.

Figure 9:
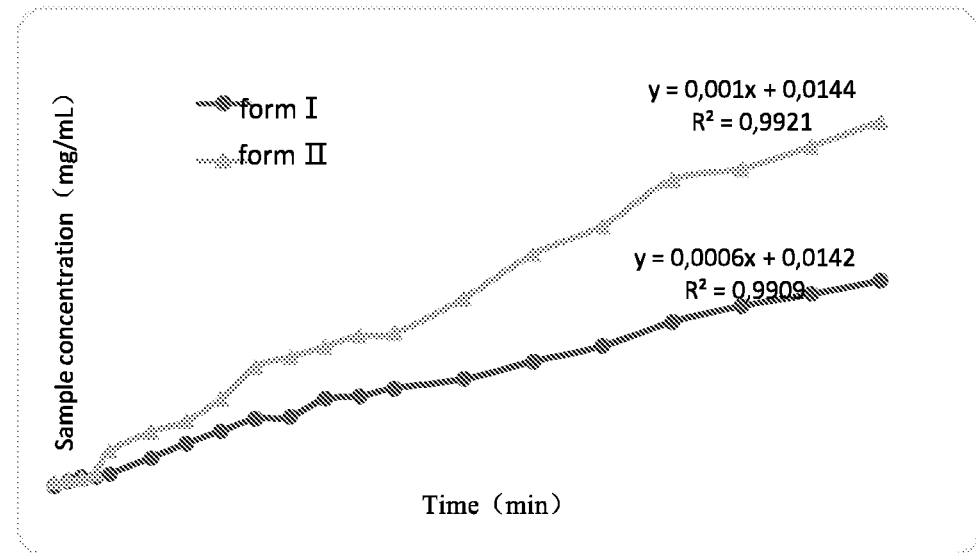
FIG. 9 provides intrinsic dissolution rate curves of the crystal forms I and II of Tasimelteon in water FIG. 10 provides the absolute configuration view of the crystal form II of Tasimelteon.

As showed in FIG. 9, the intrinsic dissolution rate of both forms was high in water, especially for crystal form II compared to crystal form I.

Example 24 Preparation of Crystal Form I Pharmaceutical Composition

The following table illustrates a single dose unit containing crystal form I in a size 00 capsule.

| Material | Percent by weight | Quantity (mg/tablet) |
| --- | --- | --- |
| Form I | 60% | 300 |
| Pregelatinized starch | 39% | 195 |
| Magnesium stearate | 1% | 5 |
| total | 100% | 500 |

The pregelatinized starch and crystal form I are passed through a 150 mesh sieve and then are loaded into a diffusion mixer and blended for 15 mins. The magnesium stearate is added to the diffusion mixer. The blend is then encapsulated in a size 00 capsule, 500 mg per capsule using a Dosator type capsule filling machine for mass production.

Example 25 Preparation of Crystal Form II Pharmaceutical Composition

The following table illustrates a single dose unit containing crystal form II in a size 00 capsule.

| Material | Percent by weight | Quantity (mg/tablet) |
| --- | --- | --- |
| Form II | 60% | 300 |
| Pregelatinized starch | 39% | 195 |
| Magnesium stearate | 1% | 5 |
| total | 100% | 500 |

The pregelatinized starch and crystal form II are passed through a 150 mesh sieve and then loaded into a diffusion mixer and blended for 15 mins. The magnesium stearate is added to the diffusion mixer. The blend is then encapsulated in a size 00 capsule, 500 mg per capsule using a Dosator type capsule filling machine.

Moreover, it is noted that, the above examples are for illustrative purposes only, and are not intended to limit the scope of the invention. Various changes and modifications apparent to those skilled in the art are also intended to fall within the scope of the appended claims.

What is claimed is:

1. A crystal form I of Tasimelteon: characterized by an X-ray powder diffraction spectrum, using CuKα radiations, and represented by a 2θ angle having diffraction peaks at least at 7.2°±0.2°, 7.9°±0.2°, 10.6°±0.2°, 14.4°±0.2°, 15.9°±0.2°, 17.3°±0.2°, 21.0°±0.2°, 23.2°±0.2, and 24.4°±0.2°.

2. A crystal form I of Tasimelteon as recited in claim 1 also exhibiting characteristic peaks in X-ray powder diffraction spectrum using CuKα radiation at diffraction angles (2θ) of about 10.8°±0.2°, 16.3°±0.2°, 16.6°±0.2°, 19.7°±0.2°, 21.3°±0.2°, 21.70°±0.2°, 24.1°±0.2°, 24.9°±0.2°, 27.8°±0.2°, 28.3°±0.2 and 30.0°±0.2°.

3. A crystal form I of Tasimelteon as recited in claim 1, characterized by a differential scanning calorimetry (DSC) plot comprising a melting endothermic event with a peak temperature of 74.2° C.; or a representative TGA plot.

4. A preparation process for a crystal form I of Tasimelteon as recited in claim 1 including the following steps:
(a) dissolving an amorphous form of Tasimelteon in an organic solvent, or mixtures of organic solvent and alkane mixed in any ratio, or mixtures of water and organic solvent at 40 to 70° C.; these solvents are used in an amount of 2 to 20 ml, with respect to 1 g of amorphous form of Tasimelteon;
(b) cooling the hot solution to 0 to 20° C. rapidly or slowly, and crystallization;
(c) suction filtering the solvent mixture and drying the polymorph in vacuum at a temperature 35 to 45° C. for 2 to 4 hours;
wherein, the organic solvent system is selected from alcohol, ketone, ester, ether and chloroform; said alcohol is selected from methanol, ethanol, propanol or a mixture of two or more thereof; said ketone is selected from acetone, methyl butyl ketone or a mixture of two or more thereof; said ester is selected from ethyl acetate, propyl acetate, or a mixture of two or more thereof; said ether is selected from tetrahydrofuran, methyl tertbutyl ether, or a mixture of two or more thereof; alkane comprising heptanes, hexane, and pentane; the mixtures of water and organic solvent, the volume ratio of water is 2% to 20%.

5. A crystal form II of Tasimelteon characterized by an X-ray powder diffraction spectrum using CuKα radiation and represented by a 2θ angle, having diffraction peaks at least at 6.8°±0.2°, 12.1°±0.2°, 12.5°±0.2°, 13.1°±0.2°, 13.6°±0.2°, 13.8°±0.2°, 15.8°±0.2°, 17.0°±0.2°, 18.4°±0.2°, 20.8°±0.2°, 24.2°±0.2°, and 24.4°±0.2°.

6. A crystal form II of Tasimelteon as recited in claim 5 also exhibiting characteristic peaks in X-ray powder diffraction spectrum using CuKα radiation at diffraction angles (2θ) of about 19.1°±0.2°, 19.9°±0.2°, 20.4°±0.2°, 23.0°±0.2°, 24.7°±0.2°, 25.3°±0.2°, 26.7°±0.2°, 27.1°±0.2° and 28.0°±0.2°.

7. A crystal form II of Tasimelteon as recited in claim 5, characterized by a differential scanning calorimetry (DSC) plot comprising an endothermic event with a peak temperature of 55.0° C.; and a further melting endothermic event, is observed with a peak temperature of 74.3° C. or a representative TGA plot.

8. A crystal form II of Tasimelteon as recited in claim 5 prepared by
(a) dissolving an amorphous form of Tasimelteon in water, or in mixtures of water and organic solvent at 40 to 70° C.; and these solvents are used in an amount of 3 to 30 ml, with respect to 1 g of amorphous form of Tasimelteon;
(b) cooling the hot solution to 0 to 25° C. slowly, and crystallization (stirring or static);
(c) filtering the solvent mixture and drying the polymorph at a temperature 35 to 45° C. for 2 to 4 hours to get a crystal form II of Tasimelteon;
wherein, the organic solvent is selected from alcohol, ketone, acetonitrile, and dimethyl sulfoxide; the mixtures of water and organic solvent, the volume ratio of organic solvent is 10% to 60%; said alcohol is selected from methanol, ethanol, propanol or a mixture of two or more thereof; said ketone is selected from acetone, methyl butyl ketone or a mixture of two or more thereof.

9. A method for the manufacture of medicaments for the treatment of Non-24-Hour Sleep-Wake Disorder, comprising the step of providing for said medicaments of a crystal form I of Tasimelteon, characterized by an X-ray powder diffraction spectrum using CuKα radiation and represented by a 2θ angle having diffraction peaks at least at 7.2°±0.2°, 7.9°±0.2°, 10.6°±0.2°, 14.4°±0.2°, 15.9°±0.2°, 17.3°±0.2°, 21.0°±0.2°, 23.2°±0.2°, and 24.4°+0.2° and/or a crystal form II of Tasimelteon, characterized by an X-ray powder diffraction spectrum using CuKα radiation and represented by a 2θ angle has diffraction peaks at least at 6.8°±0.2°, 12.1°±0.2°, 12.5°±0.2°, 13.1°±0.2°, 13.6°±0.2°, 13.8°±0.2°, 15.8°±0.2°, 17.0°±0.2°, 18.4°±0.2°, 20.8°±0.2°, 24.2°±0.2°, and 24.4°±0.2°.

10. A pharmaceutical composition comprising a crystal form I of Tasimelteon, characterized by an X-ray powder diffraction spectrum using CuKα radiation and represented by a 2θ angle having diffraction peaks at least at 7.2°±0.2°, 7.9°±0.2°, 10.6°±0.2°, 14.4°±0.2°, 15.9°±0.2°, 17.3°±0.2°, 21.0°±0.2°, 23.2°±0.2°, and 24.4°±0.2° and/or a crystal form II of Tasimelteon, characterized by an X-ray powder diffraction spectrum using CuKα radiation and represented by a 2θ angle having diffraction peaks at least at 6.8°±0.2°, 12.1°±0.2°, 12.5°±0.2°, 13.1°±0.2°, 13.6°±0.2°, 13.8°±0.2°, 15.8°±0.2°, 17.0°±0.2°, 18.4°±0.2°, 20.8°±0.2°, 24.2°±0.2°, and 24.4°±0.2° as active pharmaceutical ingredients.

11. A preparation process for a crystal form I of Tasimelteon as recited in claim 2 including the following steps:
(a) dissolving an amorphous form of Tasimelteon in an organic solvent, or in mixtures of an organic solvent and an alkane, mixed in any ratio, or mixtures of water and organic solvent at 40 to 70° C.; these solvents are used in an amount of 2 to 20 ml, with respect to 1 g of amorphous form of Tasimelteon;
(b) cooling the hot solution to 0 to 20° C. rapidly or slowly, and crystallization;
(c) suction filtering the solvent mixture and drying the polymorph in vacuum at a temperature 35 to 45° C. for 2 to 4 hours;
wherein, the organic solvent system is selected from alcohol, ketone, ester, ether and chloroform; said alcohol is selected from methanol, ethanol, propanol or a mixture of two or more thereof; said ketone is selected from acetone, methyl butyl ketone or a mixture of two or more thereof; said ester is selected from ethyl acetate, propyl acetate, or a mixture of two or more thereof; said ether is selected from tetrahydrofuran, methyl tertbutyl ether, or a mixture of two or more thereof; alkane comprising heptanes, hexane, and pentane; the mixtures of water and organic solvent, the volume ratio of water is 2% to 20%.

12. A preparation process for a crystal form I of Tasimelteon as recited in claim 3 including the following steps:
(a) dissolving an amorphous form of Tasimelteon in an organic solvent, or in mixtures of an organic solvent and an alkane, mixed in any ratio, or mixtures of water and organic solvent at 40 to 70° C.; these solvents are used in an amount of 2 to 20 ml, with respect to 1 g of amorphous form of Tasimelteon;
(b) cooling the hot solution to 0 to 20° C. rapidly or slowly, and crystallization;
(c) suction filtering the solvent mixture and drying the polymorph in vacuum at a temperature 35 to 45° C. for 2 to 4 hours;
wherein, the organic solvent system is selected from alcohol, ketone, ester, ether and chloroform; said alcohol is selected from methanol, ethanol, propanol or a mixture of two or more thereof; said ketone is selected from acetone, methyl butyl ketone or a mixture of two or more thereof; said ester is selected from ethyl acetate, propyl acetate, or a mixture of two or more thereof; said ether is selected from tetrahydrofuran, methyl tertbutyl ether, or a mixture of two or more thereof; alkane comprising heptanes, hexane, and pentane; the mixtures of water and organic solvent, the volume ratio of water is 2% to 20%.

13. A crystal form II of Tasimelteon as recited in claim 6 prepared by
(a) dissolving an amorphous form of Tasimelteon in water, or in mixtures of water and an organic solvent at 40 to 70° C.; and these solvents are used in an amount of 3 to 30 ml, with respect to 1 g of an amorphous form of Tasimelteon;
(b) cooling the hot solution to 0 to 25° C. slowly, and crystallization (stirring or static);
(c) filtering the solvent mixture and drying the polymorph at a temperature 35 to 45° C. for 2 to 4 hours to get a crystal form II of Tasimelteon;
wherein, the organic solvent is selected from alcohol, ketone, acetonitrile, and dimethyl sulfoxide; the mixtures of water and organic solvent, the volume ratio of organic solvent is 10% to 60%; said alcohol is selected from methanol, ethanol, propanol or a mixture of two or more thereof; said ketone is selected from acetone, methyl butyl ketone or a mixture of two or more thereof.

14. A crystal form II of Tasimelteon as recited in claim 7 prepared by
(a) dissolving amorphous form of Tasimelteon in water, or mixtures of water and organic solvent at 40 to 70° C.; and these solvents are used in an amount of 3 to 30 ml, with respect to 1 g of an amorphous form of Tasimelteon;
(b) cooling the hot solution to 0 to 25° C. slowly, and crystallization (stirring or static);
(c) filtering the solvent mixture and drying the polymorph at a temperature 35 to 45° for 2 to 4 hours to get a crystal form II of Tasimelteon;
wherein, the organic solvent is selected from alcohol, ketone, acetonitrile, and dimethyl sulfoxide; the mixtures of water and organic solvent, the volume ratio of organic solvent is 10% to 60%; said alcohol is selected from methanol, ethanol, propanol or a mixture of two or more thereof; said ketone is selected from acetone, methyl butyl ketone or a mixture of two or more thereof.

15. A method, comprising administering a crystal form I of Tasimelteon as recited in claim 1 to a human for the treatment of Non-24-Hour Sleep-Wake Disorder.

16. A method, comprising administering a crystal form II of Tasimelteon as recited in claim 5 to a human for the treatment of Non-24-Hour Sleep-Wake Disorder.

17. A pharmaceutical composition comprising a crystal form I of Tasimelteon as recited in claim 1 as active pharmaceutical ingredients and further comprising a pharmaceutical carrier.

18. A pharmaceutical composition comprising a crystal form II of Tasimelteon as recited in claim 5 as active pharmaceutical ingredients and further comprising a pharmaceutical carrier.

* * * * *